(12) United States Patent
Becker et al.

(10) Patent No.: US 12,370,372 B2
(45) Date of Patent: Jul. 29, 2025

(54) ELECTRICAL CONTACT FOR A MEDICAL DEVICE LEAD

(71) Applicant: Medtronic, Inc., Minneapolis, MN (US)

(72) Inventors: Damian M. Becker, Columbia Heights, MN (US); Bernard Q. Li, Plymouth, MN (US); Darren A. Janzig, Center City, MN (US); Thomas J. Conway, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 431 days.

(21) Appl. No.: 17/808,266

(22) Filed: Jun. 22, 2022

(65) Prior Publication Data
US 2023/0009502 A1   Jan. 12, 2023

Related U.S. Application Data

(60) Provisional application No. 63/219,984, filed on Jul. 9, 2021.

(51) Int. Cl.
*A61N 1/375* (2006.01)
(52) U.S. Cl.
CPC .................. *A61N 1/3752* (2013.01)
(58) Field of Classification Search
CPC .................................... A61N 1/3752
USPC ....................................... 607/116
See application file for complete search history.

(56) References Cited

U.S. PATENT DOCUMENTS

| | | | |
|---|---|---|---|
| 4,583,543 A | 4/1986 | Peers-Trevarton |
| 5,730,628 A | 3/1998 | Hawkins |
| 7,014,473 B2 | 3/2006 | Millard et al. |
| 7,559,770 B2 | 7/2009 | Di Stefano |
| 7,890,175 B1 | 2/2011 | Rey et al. |
| 8,475,180 B2 | 7/2013 | Yumi |
| 8,690,602 B2 | 4/2014 | Flaherty |
| 8,784,143 B2 | 7/2014 | Edgell et al. |

(Continued)

FOREIGN PATENT DOCUMENTS

| | | |
|---|---|---|
| JP | 2014235804 A | 12/2014 |
| WO | 1986001120 A1 | 2/1986 |
| WO | 1986006965 A1 | 12/1986 |

OTHER PUBLICATIONS

Extended Search Report from counterpart European Application No. 22183489.8 dated Nov. 15, 2022, 7 pp.

(Continued)

*Primary Examiner* — Nadia A Mahmood
(74) *Attorney, Agent, or Firm* — Shumaker & Sieffert, P.A.

(57) ABSTRACT

A electrical contact for coupling a contact of a medical lead with electronics of a medical device including a contact member having a ring shaped wall defined by a ring inner diameter and ring outer diameter, a housing having a ring shape defining an opening therein, the opening configured to receive the medical lead therein, wherein the housing is defined in part by a housing longitudinal axis and a housing inner diameter, the contact member having at least one deflectable finger extending from the ring shaped wall into a contact opening defined by the ring inner diameter of the ring shaped wall, wherein the finger extends to a distal end and has side edges, the side edges of the finger disposed at respective angles relative to the housing longitudinal axis.

21 Claims, 11 Drawing Sheets

(56) References Cited

U.S. PATENT DOCUMENTS

| | | |
|---|---|---|
| 9,300,063 B2 | 3/2016 | Tatzel et al. |
| 10,135,167 B2 | 11/2018 | Wollitzer et al. |
| 10,347,996 B2 | 7/2019 | Kung et al. |
| 10,446,963 B2 | 10/2019 | Ungerer et al. |
| 10,576,266 B2 | 3/2020 | Li et al. |
| 10,632,316 B2 | 4/2020 | Janzig et al. |
| 2002/0144900 A1 | 10/2002 | Keigler |
| 2003/0073348 A1* | 4/2003 | Ries ............ H01R 31/06 439/578 |
| 2019/0245310 A1 | 8/2019 | Medina et al. |
| 2020/0044377 A1 | 2/2020 | Uppleger |
| 2020/0155827 A1 | 5/2020 | Li et al. |

OTHER PUBLICATIONS

Response to Extended Search Report dated Nov. 14, 2022, from counterpart European Application No. 22183489.8 filed Jul. 11, 2023, 12 pp.

Sanke, "Crown Spring—DJL Crown," Product Webpage, accessed from https://sanke.vn/products/crown-spring%EF%BC%8Ddjl-crown/, retrieved on Dec. 3, 2020, 4 pp.

* cited by examiner

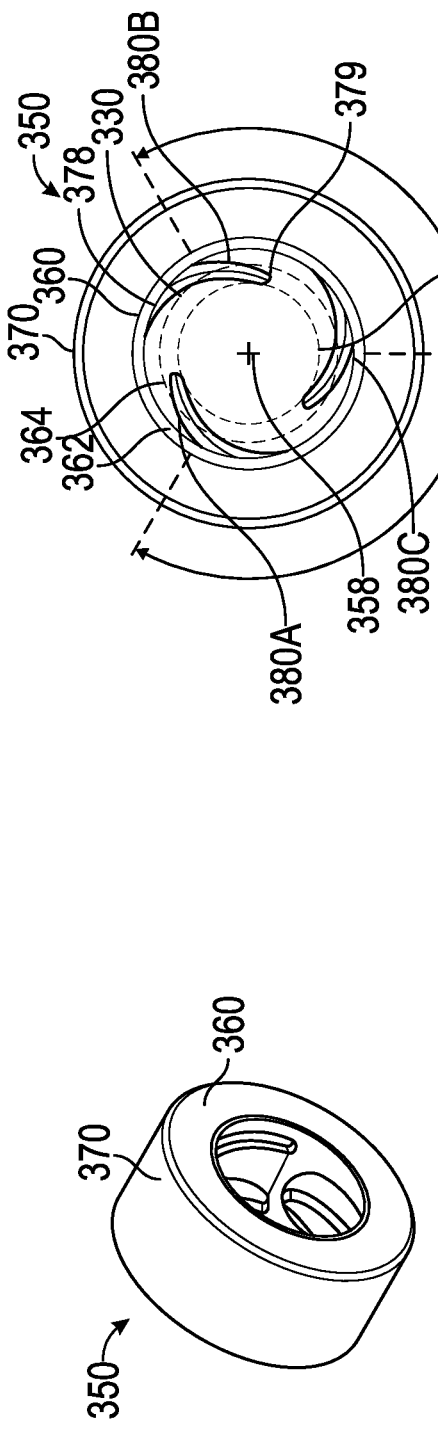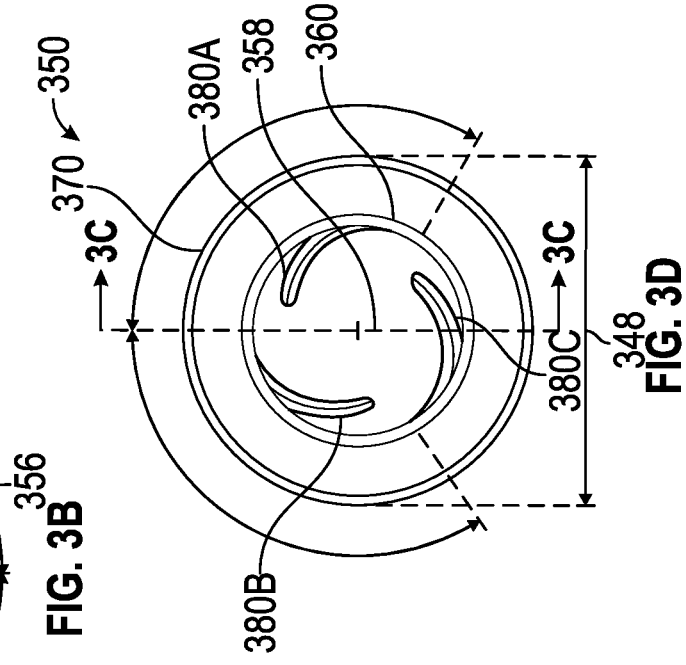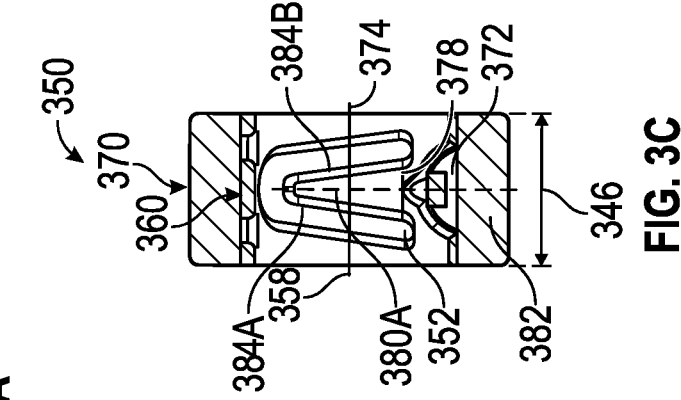

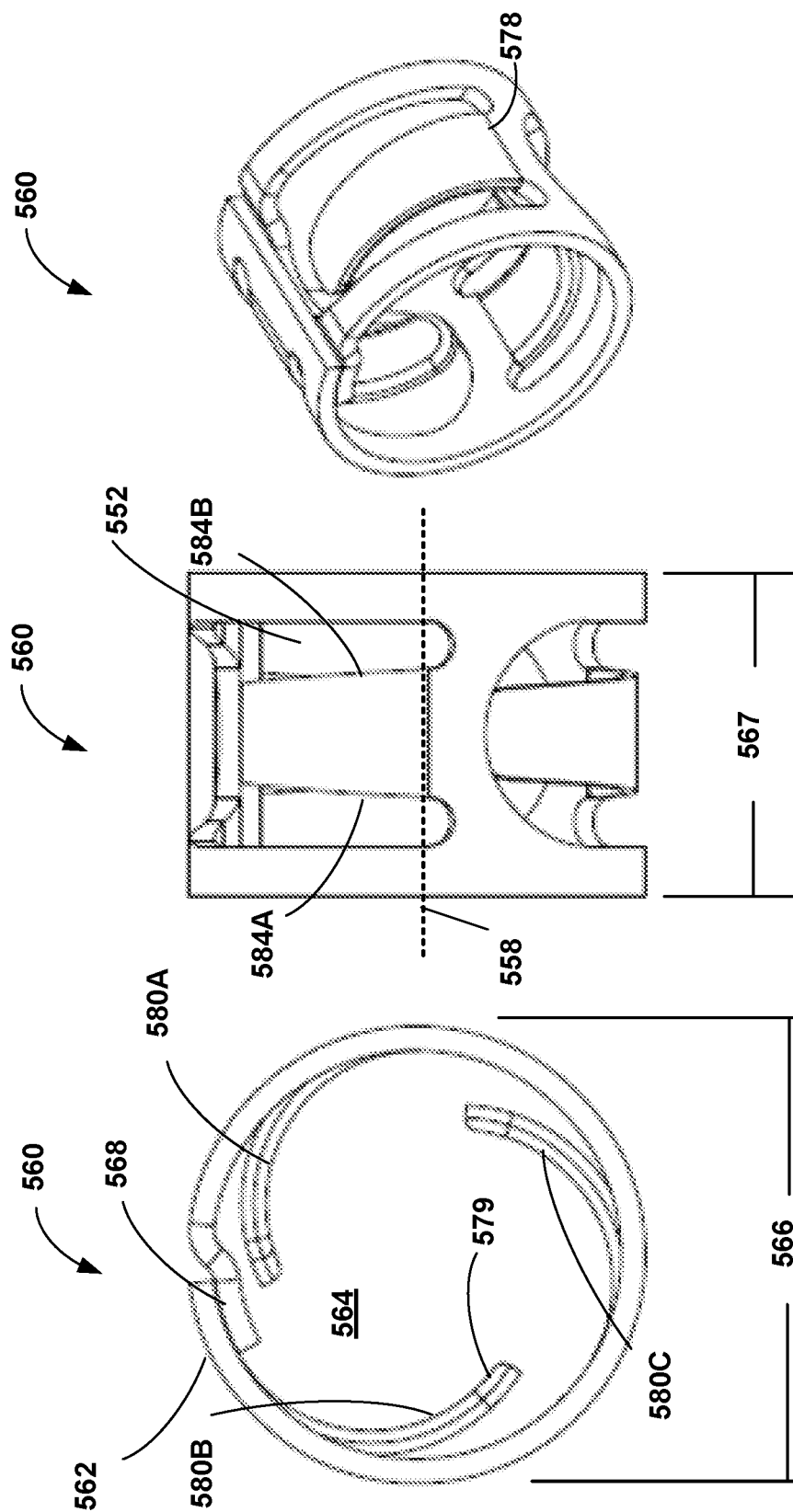

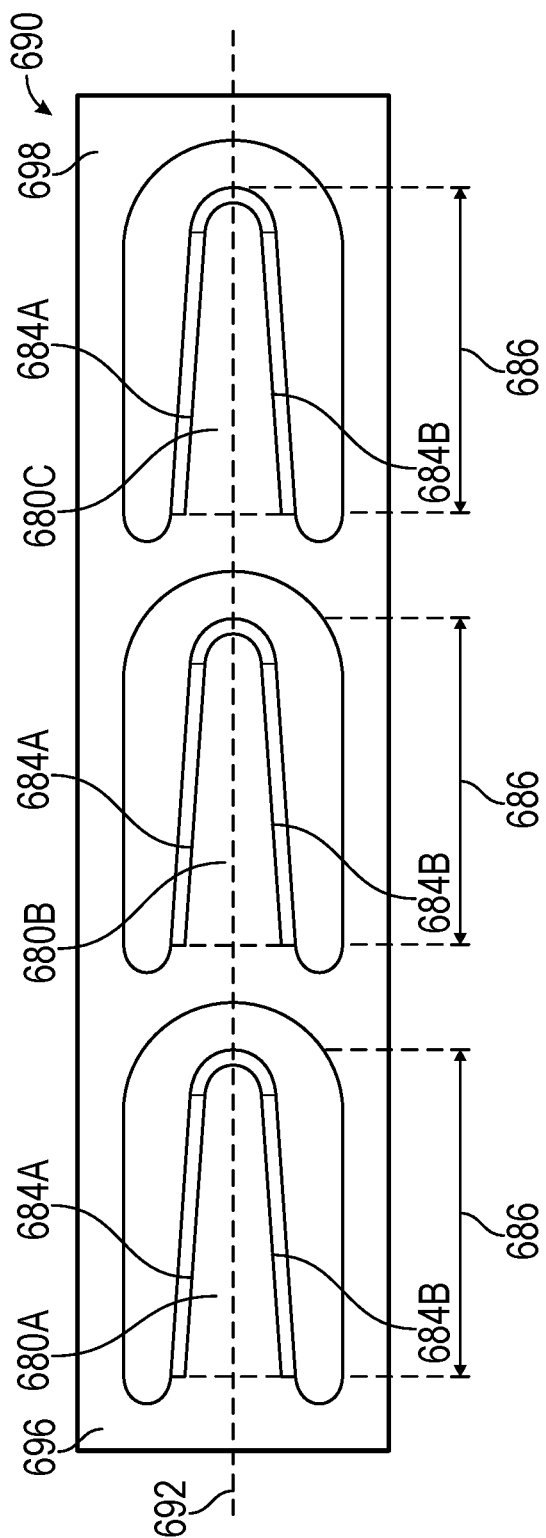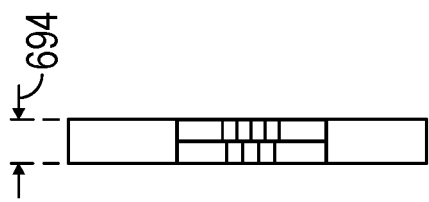
FIG. 6A
FIG. 6B

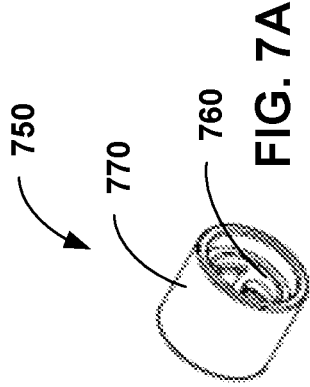
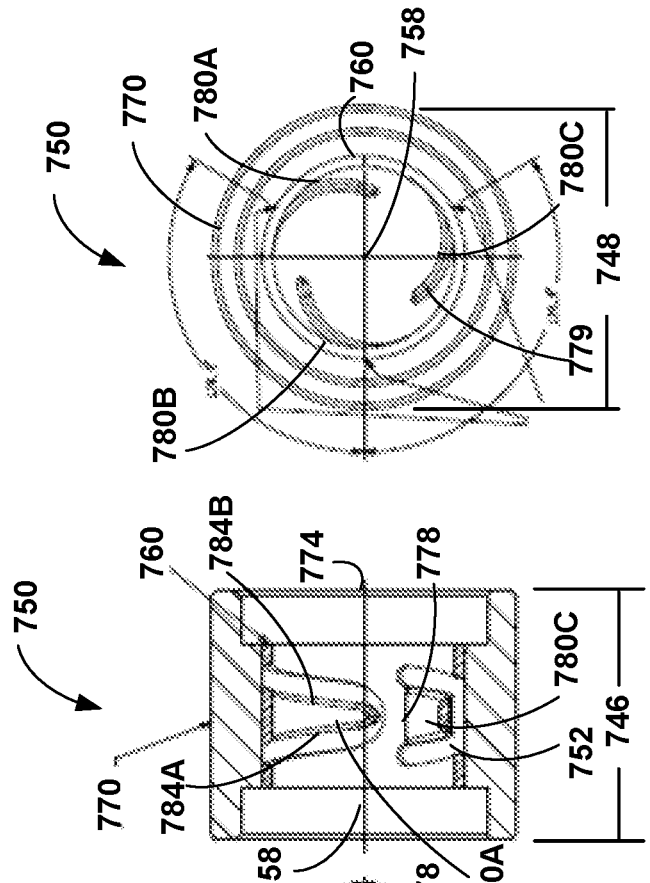
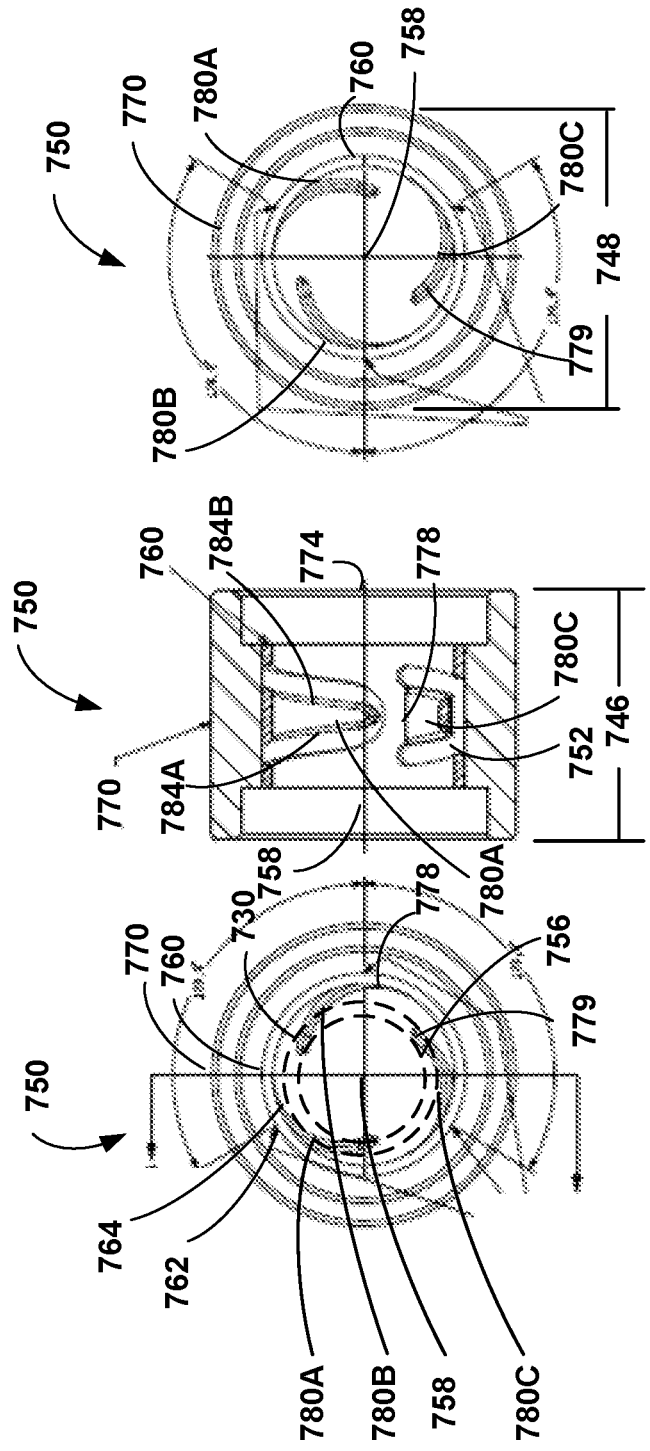

ELECTRICAL CONTACT FOR A MEDICAL DEVICE LEAD

This application claims the benefit of U.S. Provisional Patent Application No. 63/219,984, filed Jul. 9, 2021, the entire contents of which is incorporated herein by reference.

TECHNICAL FIELD

This disclosure generally relates to medical devices, and more specifically, an electrical contact for a medical device.

BACKGROUND

Electrical stimulation devices, sometimes referred to as neurostimulators or neurostimulation devices, may be external to or implanted within a patient, and configured to deliver electrical stimulation therapy to various tissue sites to treat a variety of symptoms or conditions such as chronic pain, tremor, Parkinson's disease, epilepsy, or other neurological disorders, urinary or fecal incontinence, sexual dysfunction, obesity, or gastroparesis. An electrical stimulation device may deliver electrical stimulation therapy via electrodes, e.g., carried by one or more leads. The one or more leads may be electrically coupled with an implantable medical device via a connector within the medical device.

SUMMARY

This disclosure is directed to an electrical contact for medical devices that may be configured to deliver electrical stimulation therapy. An electrical stimulation device may deliver electrical stimulation therapy via electrodes, e.g., carried by one or more leads. The one or more leads may be electrically coupled with an implantable medical device via an electrical contact within the medical device. The electrical contact may include one or more deflectable fingers configured to contact the lead. The deflectable fingers may be V-shaped, spoon shaped, or have any other shapes configured to facilitate contact with an inserted lead.

In one or more examples, an electrical contact for coupling a contact of a medical lead with electronics of a medical device includes a contact member having a ring shaped wall defined by a ring inner diameter and ring outer diameter, a housing having a ring shape defining an opening therein, the opening configured to receive the contact member therein, wherein the housing is defined in part by a housing longitudinal axis and a housing inner diameter, the contact member having at least one deflectable finger extending from the ring shaped wall into a contact opening defined by the ring inner diameter of the ring shaped wall, wherein the finger extends to a distal end and has side edges, the side edges of the finger disposed at respective angles relative to the housing longitudinal axis.

In one or more examples, an implantable medical device that is configured to deliver electrical stimulation therapy includes an electronics housing having a connector header, an electrical contact disposed within the connector header, the electrical contact configured for coupling a medical lead with electronics of a medical device configured to deliver electrical stimulation therapy, the electrical contact comprising a contact member having a ring shaped wall defined by a ring inner diameter and ring outer diameter, a housing having a ring shape defining an opening therein, the opening configured to receive the medical lead therein, wherein the housing is defined in part by a housing longitudinal axis and a housing inner diameter, the contact member having at least one deflectable finger extending from the ring shaped wall into a contact opening defined by the ring inner diameter of the ring shaped wall, the contact member defined in part by a contact longitudinal axis, the contact longitudinal axis aligned with the housing longitudinal axis, wherein the finger is defined in part by a central axis, wherein the finger extends to a distal end and has side edges, the side edges of the finger disposed at respective angles relative to the housing longitudinal axis.

In one or more examples, a method for forming an electrical contact includes stamping a contact member from a strip of material and forming at least one deflectable finger, rolling the stamped contact member into a ring shaped wall defined by a ring inner diameter and ring outer diameter, and the at least one deflectable finger extending from the ring shaped wall into a contact opening defined by the ring inner diameter of the ring shaped wall, and disposing the rolled contact member within housing of an electrical contact of for a medical device.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIG. 3A is a perspective view illustrating an electrical contact for an implantable medical device (IMD) in accordance with one or more techniques of this disclosure.

FIG. 3B is an end view illustrating an electrical contact for an implantable medical device (IMD) in accordance with one or more techniques of this disclosure.

FIG. 3C is a cross-sectional side view illustrating an electrical contact for an implantable medical device (IMD) in accordance with one or more techniques of this disclosure.

FIG. 3D is a side view illustrating an electrical contact for an implantable medical device (IMD) in accordance with one or more techniques of this disclosure.

FIG. 5A is a first end view illustrating a contact member for an electrical contact in accordance with one or more techniques of this disclosure.

FIG. 5B is a second side view illustrating a contact member for an electrical contact in accordance with one or more techniques of this disclosure.

FIG. 5C is a perspective view illustrating a contact member for an electrical contact in accordance with one or more techniques of this disclosure.

FIG. 6A is a top view of a stamped contact member in accordance with one or more techniques of this disclosure.

FIG. 6B is a side view of the stamped contact member of FIG. 6A.

FIG. 7A is a conceptual diagram illustrating an electrical contact for an implantable medical device (IMD) in accordance with one or more techniques of this disclosure.

FIG. 7B is an end view illustrating an electrical contact for an implantable medical device (IMD) in accordance with one or more techniques of this disclosure.

FIG. 7C is a cross-sectional side view illustrating an electrical contact for an implantable medical device (IMD) in accordance with one or more techniques of this disclosure.

FIG. 7D is a side view illustrating an electrical contact for an implantable medical device (IMD) in accordance with one or more techniques of this disclosure.

DETAILED DESCRIPTION

Electrical stimulation devices, sometimes referred to as neurostimulators or neuro stimulation devices, may be external to or implanted within a patient, and configured to deliver electrical stimulation therapy to various tissue sites to treat a variety of symptoms or conditions such as chronic pain, tremor, Parkinson's disease, epilepsy, or other neurological disorders, urinary or fecal incontinence, sexual dysfunction, obesity, or gastroparesis. An electrical stimulation device may deliver electrical stimulation therapy via electrodes, e.g., carried by one or more leads. The one or more leads may be electrically coupled with an implantable medical device via an electrical contact within the medical device.

An electrical contact provides an electrical interface between the lead and the implantable medical device. The electrical contact may accommodate varying sizes or diameters of the leads. The electrical contact may also provide a lower insertion force to facilitate assembly of the lead with the implantable medical device, and yet a higher contact force to facilitate electrical connection between the lead and the implantable medical device. The electrical contact may be used in a terminal of an implantable medical device which receives the lead therein. This disclosure describes electrical contacts and techniques for fabricating electrical contacts for use with medical devices.

Figure 1:
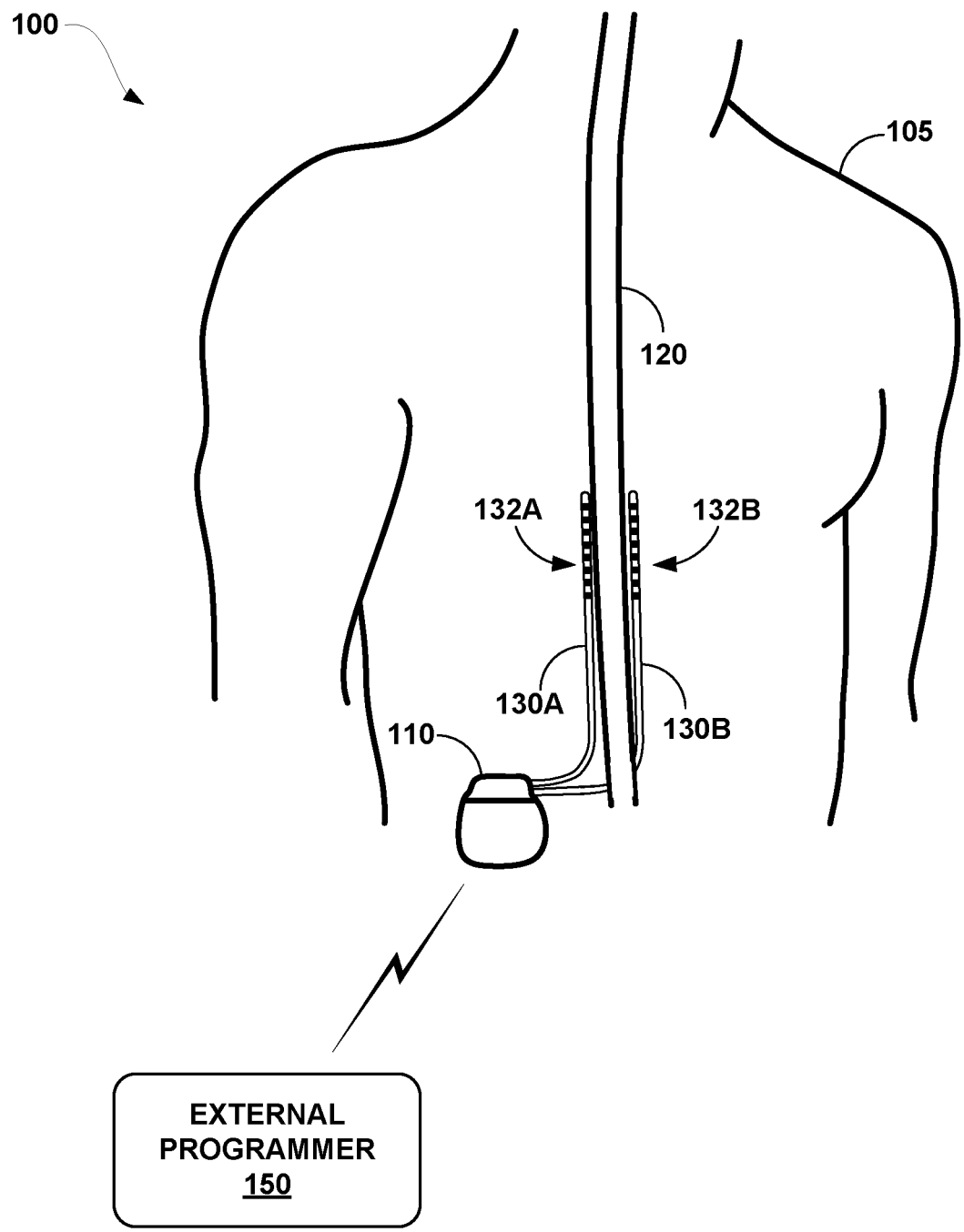
FIG. 1 is a conceptual diagram illustrating an example system that includes an implantable medical device (IMD) in the form of a neurostimulation device configured to deliver spinal cord stimulation (SCS), an external programmer in accordance with one or more techniques of this disclosure.

An electrical stimulation system may include a stimulator system that interacts with a stimulator programmer. FIG. 1 is a conceptual diagram illustrating an example system 100 that includes an implantable medical device (IMD) 110 configured to deliver spinal cord stimulation (SCS) therapy, processing circuitry 140, and an external programmer 150, in accordance with one or more examples of this disclosure. Although the examples described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of neurostimulation devices or other therapeutic applications of neuro stimulation.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105, e.g., for relief of chronic pain or other symptoms, via one or more electrodes 132A, 132B of leads 130A and/or 130B, respectively. In the example of FIG. 1, each lead 130A, 130B includes eight electrodes 132A, 132B respectively, although the leads may each have a different number of electrodes. Leads 130A, 130B may be referred to collectively as "leads 130" and electrodes 132A, 132B may be referred to collectively as electrodes 132. In other examples, IMD 110 may be coupled to a single lead carrying multiple electrodes or more than two leads each carrying multiple electrodes.

IMD 110 may be a chronic electrical stimulator that remains implanted within patient 105 for weeks, months, or years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to one or more leads percutaneously implanted within the patient. In some examples, IMD 110 uses electrodes on one or more leads, while in other examples, IMD 110 use one or more electrodes on a lead or leads and one of more electrodes on a housing of the IMD.

IMD 110 may be constructed of any polymer, metal, or composite material sufficient to house the components of IMD 110 (e.g., components illustrated in FIG. 2A, 2B) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted at other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

In the example of FIG. 1, electrical stimulation energy, which may be delivered as regulated current or regulated voltage-based pulses, is delivered from IMD 110 to one or more target tissue sites of patient 105 via leads 130 and electrodes 132. Leads 130 position electrodes 132 adjacent to target tissue of spinal cord 120. One or more of the electrodes 132 may be disposed at a distal tip of a lead 130 and/or at other positions at intermediate points along the lead. Leads 130 may be implanted and coupled to IMD 110. The electrodes 132 may transfer electrical stimulation generated by an electrical stimulation generator in IMD 110 to tissue of patient 105. Although leads 130 may each be a single lead, a lead 130 may include a lead extension or other segments that may aid in implantation or positioning of lead 130.

The electrodes 132 of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration. Deployment of electrodes via leads 130 is described for purposes of illustration, but electrodes may be arranged on a housing of IMD 110, e.g., in rows and/or columns (or other arrays or patterns), as surface electrodes, ring electrodes, or protrusions.

Neurostimulation parameters defining the electrical stimulation pulses delivered by IMD 110 through electrodes 132 of leads 130 may include information identifying which electrodes have been selected for delivery of the stimulation pulses according to a stimulation program and the polarities of the selected electrodes (the electrode combination), and voltage or current amplitude, pulse rate (i.e., frequency), and pulse width of the stimulation pulses. The neurostimulation parameters may further include a cycle parameter that specifies when, or how long, stimulation is turned on and off. Neurostimulation stimulation parameters may be programmed prior to delivery of the neurostimulation pulses, manually adjusted based on user input, or automatically controlled during delivery of the neurostimulation pulses, e.g., based on sensed conditions.

Although the example of FIG. 1 is directed to SCS therapy, e.g., to treat pain, in other examples, system 100 may be configured to treat other conditions that may benefit from neurostimulation therapy. For example, system 100 may be used to treat tremor, Parkinson's disease, epilepsy, or other neurological disorders, urinary or fecal incontinence, sexual dysfunction, obesity, or gastroparesis, or psychiatric disorders such as depression, mania, obsessive compulsive disorder, anxiety disorders, or cardiac disorders. Hence, in some examples, system 100 may be configured to deliver sacral neuromodulation (SNM), deep brain stimulation (DBS), peripheral nerve stimulation (PNS), or other stimulation, such as peripheral nerve field stimulation (PNFS), cortical stimulation (CS), gastrointestinal stimulation, or any other stimulation therapy capable of treating a condition of patient 105. In some examples, system 100 may be configured where the electrical stimulation includes parameters to deliver therapy to address a condition of one or more of painful diabetic neuropathy (PDN), peripheral vascular disease (PVD), peripheral artery disease (PAD), complex regional pain syndrome (CRPS), leg pain, back pain or pelvic pain.

Leads 130 may include, in some examples, one or more sensors configured to sense one or more physiological parameters of patient 105, such as patient activity, pressure, temperature, posture, heart rate, or other characteristics. At least some of electrodes 132 may be used to sense electrical signals within patient 105, additionally or alternatively to delivering stimulation. IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions.

Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may reduce the perception of pain by patient 105, and thus, provide efficacious therapy results. In some examples, some electrical stimulation pulses may be directed to glial cells while other electrical stimulation (e.g., delivered by a different electrode combination) is directed to neurons.

IMD 110 generates and delivers electrical stimulation therapy to a target stimulation site within patient 105 via the electrodes of leads 130 to patient 105 according to one or more therapy stimulation programs. A therapy stimulation program specifies values for one or more parameters that define an aspect of the therapy delivered by IMD 110 according to that program. For example, a therapy stimulation program that controls delivery of stimulation by IMD 110 in the form of stimulation pulses may define values for voltage or current pulse amplitude, pulse width, and pulse rate (e.g., pulse frequency) for stimulation pulses delivered by IMD 110 according to that program, as well as the particular electrodes and polarities forming an electrode combination used to deliver the stimulation pulses.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy. For example, external programmer 150 may transmit therapy stimulation programs, stimulation parameter adjustments, therapy stimulation program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

IMD 110 and external programmer 150 may exchange information and may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

IMD 110, in response to commands from external programmer 150, may deliver electrical stimulation therapy according to a plurality of therapy stimulation programs to a target tissue site of a patient via of the spinal cord 120 of patient 105 via electrodes on leads 130. In some examples, IMD 110 automatically modifies therapy stimulation programs as therapy needs of patient 105 evolve over time. For example, the modification of the therapy stimulation programs may cause the adjustment of at least one parameter of the plurality of stimulation pulses based on received information.

Figure 2A:
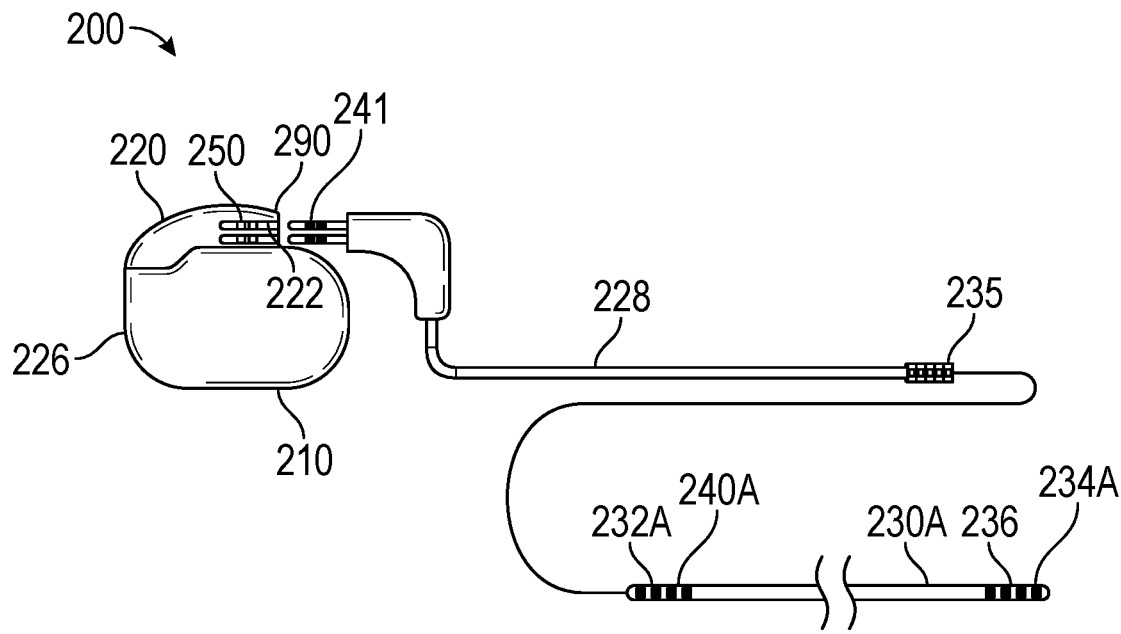
FIG. 2A is a side view illustrating an example system that includes an implantable medical device (IMD) in accordance with one or more techniques of this disclosure.

FIG. 2A shows an IMD 210 which may be an implantable electrical stimulator that is configured to generate and deliver electrical stimulation therapy to patient for relief of symptoms, via one or more electrodes 236. IMD 210 may be a chronic electrical stimulator that remains implanted within a patient for weeks, months, or years. In other examples, IMD 210 may be a temporary, or trial, stimulator used to screen or evaluate the efficacy of electrical stimulation for chronic therapy. In one example, IMD 210 is implanted within a patient, while in another example, IMD 210 is an external device coupled to one or more leads percutaneously implanted within the patient. In some examples, IMD 210 uses electrodes on one or more leads, while in other examples, IMD 210 use one or more electrodes on a lead or leads and one of more electrodes on a housing of the IMD.

IMD 210 may include an electronics housing 226 having a connector header 220. One or more connector channels 290 may be disposed within the connector header 220. Each connector channel may include one or more electrical contacts 250 and, typically, a plurality of electrical contacts. The electrical contact 250 may be configured for coupling an extension 228 with electronics of IMD 210 configured to deliver electrical stimulation therapy. A distal end 235 of extension 228 may be electrically coupled with a proximal end 232A of lead 230A to electrically connect the IMD 210 with the lead 230A. The electronics housing 226 and/or header 220 may be constructed of any polymer, metal, or composite material sufficient to house the components of IMD 210. In this example, IMD 210 may be constructed with a biocompatible housing, such as titanium or stainless steel, or a polymeric material such as silicone, polyurethane, or a liquid crystal polymer, and surgically implanted at a site in a patient near the pelvis, abdomen, or buttocks. In other examples, IMD 210 may be implanted at other suitable sites within a patient, which may depend, for example, on the target site within the patient 105 the delivery of electrical stimulation therapy. The outer housing of IMD 210 may be configured to provide a hermetic seal for components, such as a rechargeable or non-rechargeable power source. In addition, in some examples, the outer housing of IMD 210 is selected from a material that facilitates receiving energy to charge the rechargeable power source.

IMD 210 may provide therapy to one or more target tissue sites of the patient via lead 230A and electrodes 236. Lead 230A may extend from a proximal end 232A to a distal end 234A. One or more of the electrodes 236 may be disposed at a distal end 234A of the lead 230A and/or at other positions at intermediate points along the lead. One or more proximal lead contacts 240A may be disposed at the proximal end 232A of the lead 230A. Lead 230A may be implanted and coupled to distal end 235 of extension 228. Proximal end 229 of the extension 228 may be coupled with IMD 210 at the proximal end 232 of the lead 230, and proximal contacts 241 may electrically couple with respective electrical contacts within a connector channel 250 within the connector header 220.

Figure 2B:
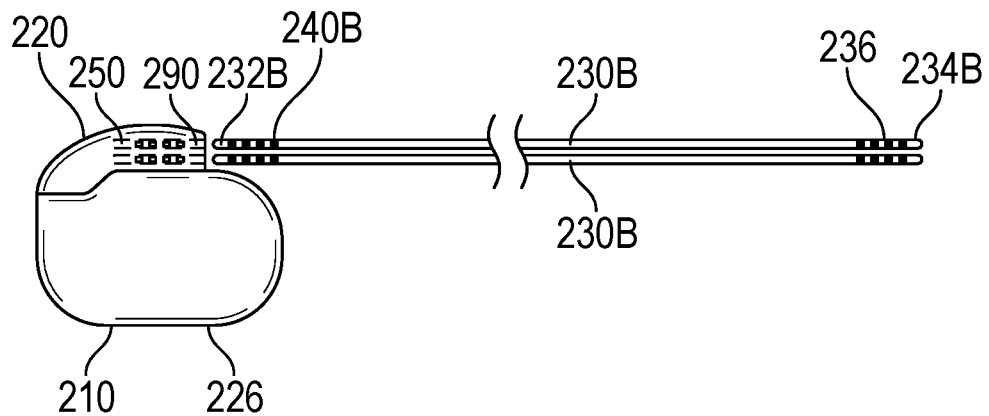
FIG. 2B is a side view illustrating an example system that includes an implantable medical device (IMD) in accordance with one or more techniques of this disclosure.

FIG. 2B shows an IMD 210 which may be an implantable electrical stimulator that is configured to generate and deliver electrical stimulation therapy to patient for relief of symptoms, via one or more electrodes 236. IMD 210 may be a chronic electrical stimulator that remains implanted within a patient for weeks, months, or years. In other examples, IMD 210 may be a temporary, or trial, stimulator used to screen or evaluate the efficacy of electrical stimulation for chronic therapy. In one example, IMD 210 is implanted within a patient, while in another example, IMD 210 is an external device coupled to one or more leads percutaneously implanted within the patient. In some examples, IMD 210 uses electrodes on one or more leads, while in other examples, IMD 210 use one or more electrodes on a lead or leads and one of more electrodes on a housing of the IMD.

IMD 210 may include an electronics housing 226 having a connector header 220. One or more connector channels 290 may be disposed within the connector header 220. Each connector channel may include one or more electrical contacts and, typically, a plurality of electrical contacts. An electrical contact 250 may be configured for coupling medical leads 230B with electronics of IMD 210 configured to deliver electrical stimulation therapy, where FIG. 2B shows two medical leads. The housing 226 and/or header 220 may be constructed of any polymer, metal, or composite material sufficient to house the components of IMD 210. In this example, IMD 210 may be constructed with a biocompatible housing, such as titanium or stainless steel, or a polymeric material such as silicone, polyurethane, or a liquid crystal polymer, and surgically implanted at a site in a patient near the pelvis, abdomen, or buttocks. In other examples, IMD 210 may be implanted at other suitable sites within a patient, which may depend, for example, on the target site within the patient 105 the delivery of electrical stimulation therapy. The outer housing of IMD 210 may be configured to provide a hermetic seal for components, such as a rechargeable or non-rechargeable power source. In addition, in some examples, the outer housing of IMD 210 is selected from a material that facilitates receiving energy to charge the rechargeable power source.

IMD 210 may provide therapy to one or more target tissue sites of the patient via leads 230B and electrodes 236. Lead 230 may extend from a proximal end 232B to a distal end 234B. One or more of the electrodes 236 may be disposed at a distal end 234B of the lead 230B and/or at other positions at intermediate points along the lead. One or more proximal lead contacts 240B may be disposed at the proximal end 232B of the leads 230B. Leads 230B may be implanted and coupled to IMD 210 at the proximal end 232B of the leads 230B, and proximal contacts 240B may electrically couple with respective electrical contacts within a connector channel 250 within the connector header 220.

Figure 2C:
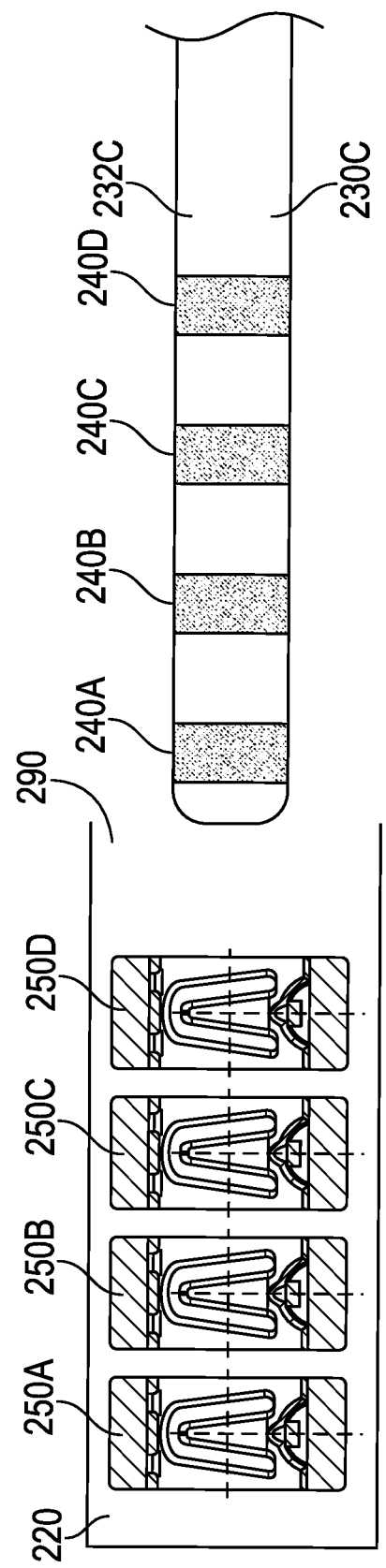
FIG. 2C is an enlarged view illustrating a portion of a header and a portion of a lead in accordance with one or more techniques of this disclosure.

FIG. 2C shows a connector channel 290 of connector header 220 with four electrical contacts 250A, 250B, 250C, 250D disposed within the header 220. The four electrical contacts 250A, 250B, 250C, 250D may be disposed in a row in the connector channel 290 so as to be positioned to receive a proximal end 232 of a lead 230C and align with four respective proximal lead contacts 240A, 240B, 240C, 240D of the lead 230C to electrically connect them to respective circuitry terminals. In some examples, each electrical contact 250 may include one, two, three, or more fingers configured to extend radially inward from an inner surface of the contact. The finger may be V-shaped, or a narrowing width moving towards the distal end, as shown in the example of FIG. 2C. In other examples, the finger may have different widths along the length of the finger. In one example, the finger includes a rounded end and a neck proximal from the rounded end, wherein the neck is narrower than the rounded end, and wherein the rounded end comprises a curved surface. This neck and rounded end with a curved surface may be referred to as a spoon shaped finger.

As shown in FIG. 2A-2C, the proximal end of the lead or lead extension may be inserted into an axial connector channel of connector header 220, such that respective proximal lead contacts engage with respective electrical contacts within the channel. For example, upon insertion of the proximal end of the lead within the axial connector channel, the proximal lead contacts arranged at different axial positions along the length of the lead engage respective electrical contacts arranged at different axial positions within the connector channel. The positioning and spacing, i.e., pitch, of the proximal lead contacts may correspond identically or partially to the positioning and spacing of the electrical contacts within the connector channel of the header. In this manner, the electrical contacts may electrically couple respective proximal lead contacts to respective terminals of circuitry within IMD 210. The proximal lead contacts, in turn, couple respective distal lead electrodes to the terminals via conductors within the lead body. The electrical contacts may be configured in accordance with various examples of this disclosure.

FIGS. 3A-3D illustrate an example electrical contact 350 configured to be disposed within the connector header 220 of the IMD 210 of FIGS. 2A-2C. In some examples, electrical contact 350 may be one of a plurality of electrical contacts arranged at various axial positions along a longitudinal axis of a connector channel of connector header 220. The electrical contact 350 provides an electrical connection between the IMD 210 and the lead 230. Electrical contact 350 may be defined in part by a length 346 and an outer diameter 348. In some examples, the length 346 to diameter 348 ratio may be 2:1. In some examples, the length 346 to diameter 348 ratio may be 2:1 or greater. In some examples, the length 346 to diameter 348 ratio may be 1:2. In some examples, electrical contact 350 may have a contact member 360 and a housing 370. Housing 370 may have a ring shape and may further having a housing interior 372 and defined in part by longitudinal axis 374. The housing interior 372 of the housing 370 may be configured to receive the contact member 360 therein. FIG. 3B shows a first end of the electrical contact 350, and FIG. 3D shows a second end of the electrical contact 350. In some examples, the electrical contact 350 may receive the proximal end of the lead from either end.

The contact member 360 may have a general ring shape having a ring shaped wall 362 defined in part by an inner diameter and an outer diameter, and may be further defined by a contact longitudinal axis 358. In some examples, contact longitudinal axis 358 may be aligned with the housing longitudinal axis 374.

Contact member 360 may include at least one deflectable finger 380 extending from the ring shaped wall 362 at a hinge portion 378 to a distal end 379. The at least one deflectable finger 380 may be coupled with the ring shaped wall 362 at the hinge portion 378, and the at least one deflectable finger 380 may pivot along at least the hinge portion 378. In some examples, the at least one deflectable finger 380 may deflect along the finger itself. In some examples, the at least one deflectable finger 380 may have a curved shape. In some examples, the at least one deflectable finger 380 may have a radius of about 0.025 inches (0.635 mm). In some examples, a clearance gap 352 may surround a portion of the at least one deflectable finger 380, as shown in FIG. 3C. In some examples, the distal end 379 of the at least one deflectable finger 380 may be disposed away from ring shaped wall 362 toward the contact longitudinal axis 358, and the distal end 379 may extend into the contact opening 364. In some examples, contact member 360 may include at least one deflectable V-shaped finger 380 extending from the ring shaped wall 362 into the contact opening 364, and having side edges 384A, 384B. In some examples, contact member 360 may include at least two deflectable V-shaped fingers. In some examples, contact member 360 may include at least three deflectable V-shaped fingers. In some examples, side edges 384A, 384B may be disposed at an angle relative to a central axis 382 of the at least one deflectable V-shaped finger 380. In some examples, the at least one deflectable V-shaped finger 380 is defined in part by a central axis 382, and the central axis is perpendicular to the housing longitudinal axis 374. In some examples, side edges 384A, 384B may be disposed at an angle relative to the housing longitudinal axis 374. In some examples, one or more side edges 384A, 384B may be disposed at a 45 degree angle to an insertion direction of the lead into the electrical contact, where the insert direction may be aligned with the contact longitudinal axis 158. In some examples, one or more side edges 384A, 384B may be disposed at a 30-60 degree angle to an insertion direction of the lead into the electrical contact, where the insert direction may be aligned with the contact longitudinal axis 158. In some examples, one or more side edges 384A, 384B may have a chamfer. In some examples, one or more side edges 384A, 384B may by rounded.

In some examples, contact member 360 may include three deflectable V-shaped fingers 380A, 380B, 380C that extend from ring shaped wall 362 into contact opening 364. In some examples, three V-shaped fingers 380A, 380B, 380C are self-centering for a lead inserted into the electrical contact. In some examples, the three V-shaped fingers 380A, 380B, 380C are symmetrically disposed around the ring shaped wall 362. In some examples, the at least one deflectable V-shaped finger 380 comprises at least two deflectable V-shaped fingers that are self-centering for leads inserted into the electrical contact 350. In one or more examples, the deflectable V-shaped finger 380 has a spring bias configured to bias the finger 380 against a contact 240 (FIG. 2) of the lead 330. In some examples, the V-shaped finger 380 extends from a hinge portion 378 to a distal portion 379, where the distal portion 379 is configured to contact the proximal lead contact 240 of the lead 330. In some examples, V-shaped fingers may extend to a distal end 379, and the distal ends 379 may extend away from wall 362 toward the contact longitudinal axis 358 and may define a distal end diameter 356. In some examples, the distal end diameter 356 may be smaller than an outer diameter of lead 330. In some examples, the lead 330 may deflect the distal end 379 of V-shaped fingers 380A, 380B, 380C toward wall 362. In some examples, V-shaped finger 380 has an elastic limit higher than 0.9% and a modulus less than 13000 ksi. In some examples, V-shaped finger 380 has an elastic limit higher than 0.9% and a modulus less than 12000-14000 ksi.

In some examples, contact member 360 is a stamped contact member. For example, the contact member 360 may be formed by stamping a strip of material into the contact member. In some examples, contact member 360 may be formed of one or more of titanium alloy or beta Ti alloy material, such as beta Ti alloy strip.

Figure 4A:
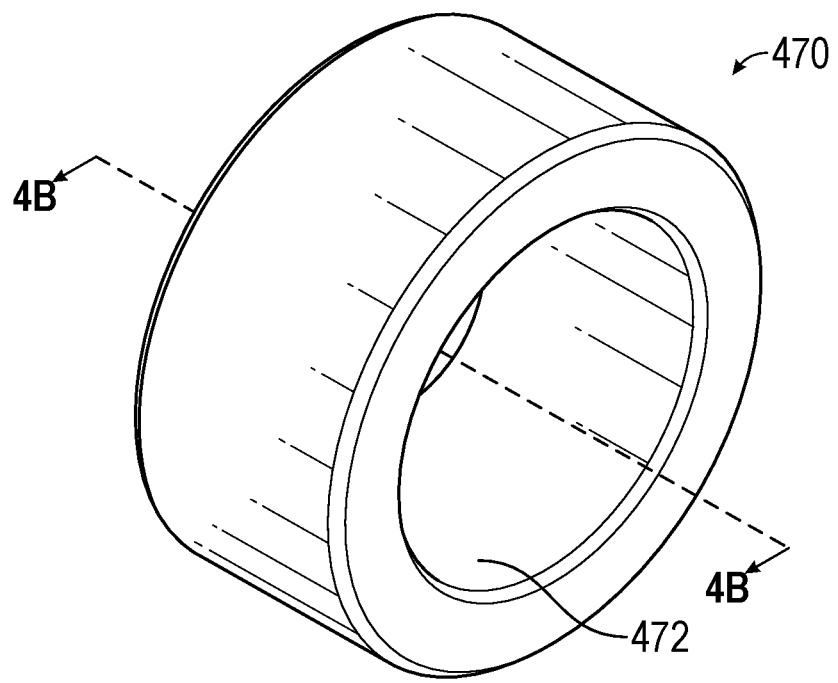
FIG. 4A is a conceptual diagram illustrating a housing for an electrical contact for an implantable medical device (IMD) in accordance with one or more techniques of this disclosure.
Figure 4B:
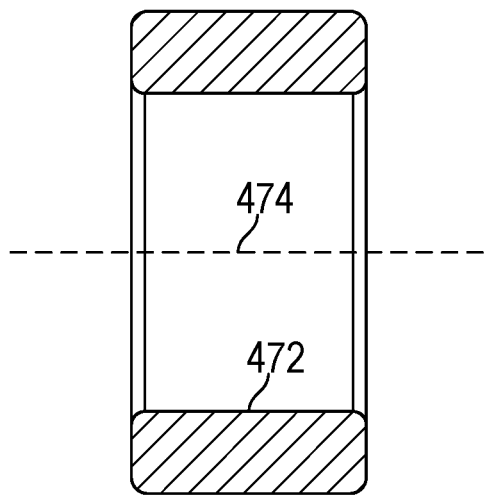
FIG. 4B is a cross-sectional side view illustrating a housing for an electrical contact for an implantable medical device (IMD) in accordance with one or more techniques of this disclosure.

FIGS. 4A and 4B illustrate an example housing 470. Housing 470 may have a ring shape and may further have a housing interior 472 and defined in part by longitudinal axis 474. The housing interior 472 of the housing 470 may be configured to receive the contact member 360 (FIG. 3C), and the longitudinal axis 474 may be aligned with a longitudinal axis of the contact member. In some examples, housing 470 may be modified to accommodate varying lengths of the contact member.

FIGS. 5A, 5B, 5C illustrate an example contact member 560. The contact member 560 may have a general ring shape having a ring shaped wall 562 defined in part by an inner diameter and an outer diameter, and may be further defined by a contact longitudinal axis 558. Contact member 560 may be disposed within housing 470 (FIGS. 4A and 4B). In some examples, contact longitudinal axis 558 may be aligned with the housing longitudinal axis 474 (FIG. 4B).

Contact member 560 may include at least one deflectable finger 580 extending from the ring shaped wall 562 at a hinge portion 578 to a distal end 579. The at least one deflectable finger 580 may be coupled with the ring shaped wall 562 at the hinge portion 578, and the at least one deflectable finger 580 may pivot along at least the hinge portion 578. In some examples, the at least one deflectable finger 580 may deflect along the finger itself. In some examples, the at least one deflectable finger 580 may have a curved shape. In some examples, a clearance gap 552 may surround a portion of the at least one deflectable finger 580, as shown in FIG. 5B. In some examples, the distal end 579 of the at least one deflectable finger 580 may be disposed away from ring shaped wall 562 toward the contact longitudinal axis 558, and the distal end 579 may extend into the contact opening 564. In some examples, contact member 560 may include at least one deflectable V-shaped finger 580 extending from the ring shaped wall 562 into the contact opening 564, and having side edges 584A, 584B. In some examples, side edges 584A, 584B may be disposed at an angle relative to a central axis 582 of the at least one deflectable V-shaped finger 580. In some examples, the at least one deflectable V-shaped finger 580 is defined in part by a central axis 582, and the central axis is perpendicular to the housing longitudinal axis 574. In some examples, side edges 584A, 584B may be disposed at an angle relative to the housing longitudinal axis. In some examples, one or more side edges 584A, 584B may be disposed at a 45 degree angle to an insertion direction of the lead into the electrical contact, where the insertion direction may be aligned with the contact longitudinal axis 558.

In some examples, contact member 560 may include at least one deflectable V-shaped finger that extends from ring shaped wall 562 into contact opening 564. In some examples, the V-shaped finger may have the shape of the letter "V". In some examples, the V-shaped finger may have side edges that taper to a point. In some examples, contact member 560 may include at least two deflectable V-shaped fingers that extend from ring shaped wall 562 into contact opening 564. In some examples, contact member 560 may include three deflectable V-shaped fingers 580A, 580B, 580C that extend from ring shaped wall 562 into contact opening 564. In some examples, three V-shaped fingers 580A, 580B, 580C are self-centering for a lead inserted into the electrical contact. For example, fingers 580A, 580B, 580C may be positioned and configured to guide the longitudinal axis of the lead into substantial alignment with the longitudinal axis 558 of the electrical contact. In some examples, the three V-shaped fingers 580A, 580B, 580C are symmetrically disposed around the ring shaped wall 562. In some examples, the at least one deflectable V-shaped finger 580 comprises at least two deflectable V-shaped fingers that are self-centering for leads inserted into the electrical contact 550. In one or more examples, the deflectable V-shaped finger 580 has a spring bias configured to bias the finger 580 against a contact 240 (FIG. 2) of the lead 230, thereby providing contact pressure for reliable electrical interconnection. In some examples, the V-shaped finger 580 extends from a hinge portion 578 to a distal portion 579, where the distal portion 579 is configured to contact the contact 240 of the lead 230. In some examples, V-shaped finger 580 has an elastic limit higher than 0.9% and a modulus less than 13000 ksi. In some examples, contact member 560 is a stamped contact member. For example, the contact member 560 may be formed by stamping a strip of material into the contact member. In some examples, contact member 560 may be formed of one or more of titanium alloy or beta Ti alloy material, such as beta Ti alloy strip. The beta Ti alloy may contain alloy elements such as Mo, Nb, Ta, Sn and Zr. The alloy can be Ti-15Mo, beta 21S, Ti15Mo5Zr3Al, beta C etc. The beta Ti alloy strip has to have beta phase fraction larger than 94%. The thickness of the beta Ti alloy strip is between 0.003" to 0.004" (about 0.076 mm to 0.102 mm). In some examples, the contact member 560 has an overlapping joint 568 where a first end of the contact member 560 overlaps a second end of the contact member 560. In some examples, contact member 560 may be defined by a length 567 and a diameter 566, and a ratio of the length to diameter is less than 1:1. In some examples, contact member 560 may be defined by a length 567 and a diameter 566, and a ratio of the length to diameter is less than 1:2.

Figures 5D, 5E, 5F:
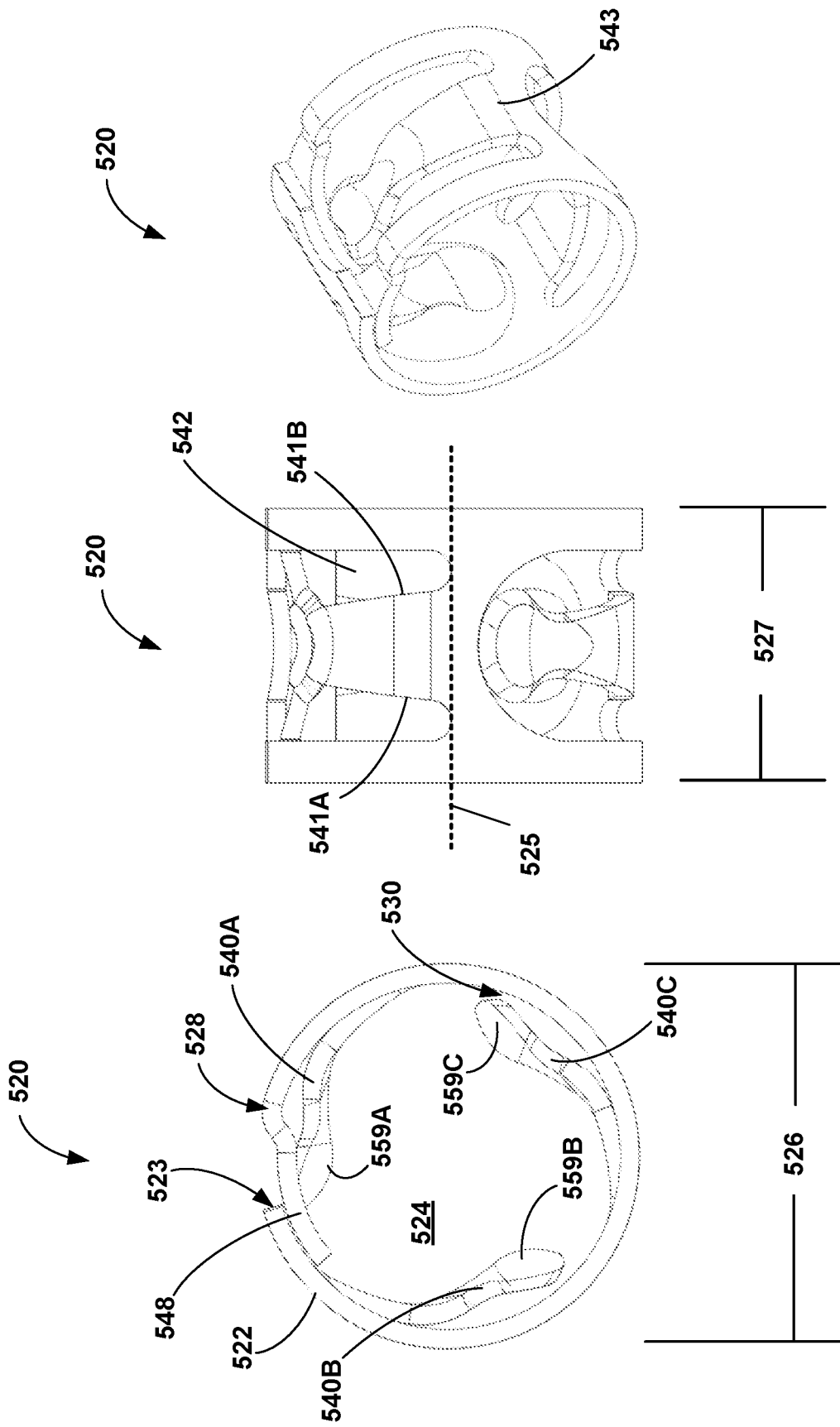
FIG. 5D is a first end view illustrating a contact member for an electrical contact in accordance with one or more techniques of this disclosure.
FIG. 5E is a second side view illustrating a contact member for an electrical contact in accordance with one or more techniques of this disclosure.
FIG. 5F is a perspective view illustrating a contact member for an electrical contact in accordance with one or more techniques of this disclosure.

FIGS. 5D, 5E, and 5F illustrate an example contact member 520. Contact member 520 may be similar to contact member 560 of FIGS. 5A-5C, but contact member 520 may have spoon shaped fingers instead of a V-shaped finger. FIG. 5D is an end view illustrating contact member 520 for an electrical contact in accordance with one or more techniques of this disclosure.

As shown in FIG. 5D, contact member 520 may have a general ring shape having a ring shaped wall 522 defined in part by an inner diameter and an outer diameter, and may be further defined by a contact longitudinal axis 525. Contact member 520 may be configured to be disposed within housing 470 (FIGS. 4A and 4B). In some examples, contact longitudinal axis 525 may be aligned with the housing longitudinal axis 474 (FIG. 4B).

Contact member 520 may include at least one deflectable finger 540 (e.g., deflectable fingers 540A, 540B, and 540C) extending radially inward from the ring shaped wall 522 at a respective hinge portion 543 to a neck portion and then a respective distal end 559 (e.g., distal ends 559A, 559B, and 559C). The distal end 559 may have a rounded width and a curved surface having the outside of the curved surface facing radially inward. The width of the neck portion being narrower than the width of the rounded distal end 559. The at least one deflectable finger 540 may be coupled with the ring shaped wall 522 at the hinge portion 543, and the at least one deflectable finger 540 may pivot along at least the hinge portion 543. In some examples, the at least one deflectable finger 540 may deflect along the finger itself. In some examples, the at least one deflectable finger 540 may have a curved shape, such as a curve in the radially inward direction. In some examples, a clearance gap 542 may surround a portion of the at least one deflectable finger 540, as shown in FIG. 5E. In some examples, the distal end 559 of the at least one deflectable finger 540 may be disposed away from ring shaped wall 522 toward the contact longitudinal axis 525, and the distal end 559 may extend into the contact opening 524. In some examples, contact member 520 may include at least one deflectable spoon shaped finger 540 extending from the ring shaped wall 522 into the contact opening 524, and having side edges 541A, 541B. As shown, spoon shaped fingers 540 include a rounded end 559 and a neck proximal from the rounded end 559, wherein the neck is narrower than the rounded end 559, and wherein the rounded end 559 comprises a curved surface. The spoon shape of fingers 540 may provide a ramped surface to facilitate the insertion of the lead through contact member 520 and ramp up finger deflection as the lead is inserted.

In some examples, side edges 541A, 541B may be disposed at an angle relative to a central axis 525 of the at least one deflectable spoon shaped finger 540. In some examples, the at least one deflectable spoon shaped finger 540 is defined in part by a central axis, and the central axis is perpendicular to the housing longitudinal axis that runs through the center lumen defined by ring shaped wall 522. In some examples, side edges 541A, 541B may be disposed at an angle relative to the housing longitudinal axis. In some examples, one or more side edges 541A, 541B may be disposed at a 45 degree angle to an insertion direction of the lead into the electrical contact, where the insertion direction may be aligned with the contact longitudinal axis 525. In some examples, side edges 541A, 541B may have a formed or stamped edge that facilitates lead insertion through reduced insertion forces as compared to a rounded or coined edge.

In some examples, the spoon shaped finger may have side edges that taper to a point. In some examples, contact member 520 may include at least two deflectable spoon shaped fingers that extend from ring shaped wall 522 into contact opening 524. In some examples, contact member 520 may include three deflectable spoon shaped fingers 540A, 540B, 540C that extend from ring shaped wall 522 into contact opening 524 In some examples, three spoon shaped fingers 540A, 540B, 540C are self-centering for a lead inserted into the electrical contact. For example, fingers 540A, 540B, 540C may be positioned and configured to guide the longitudinal axis of the lead into substantial alignment with the longitudinal axis 525 of the electrical contact. In some examples, the three spoon shaped fingers 540A, 540B, 540C are symmetrically disposed around the ring shaped wall 522. In some examples, the at least one deflectable spoon shaped finger 580 comprises at least two deflectable spoon shaped fingers that are self-centering for leads inserted into the electrical contact 520. In one or more examples, the deflectable spoon shaped finger 540 has a spring bias configured to bias the finger 540 against a contact 240 (FIG. 2) of the lead 230, thereby providing contact pressure for reliable electrical interconnection. The deflectable finger 540 may be formed with a gap 530 between the radially outside edge of finger 540 and the housing when inserted. The gap 530 may be smaller than in the V-shaped finger 580 which may reduce or prevent overstraining finger 540 when insertion of the lead causes finger 540 to bend radially outward. In some examples, the size of gap 530 may in the range of about 0.05 mm to about 0.25 mm, but may be in a range of about 0.010 mm to about 0.013 mm, prior to lead insertion. The size of gap 530 may be dependent on several factors, such as finger length, finger thickness, and material selection. In some examples, the spoon shaped finger 540 extends from a hinge portion 543 to a distal portion 559, where the distal portion 559 is configured to contact the contact 240 of the lead 230.

In some examples, the length of deflectable finger 540 may selected to be as long as possible without interfering with the next finger around the circumference of ring shaped wall 522. In some examples, the thickness of deflectable finger 540 may be selected to achieve a target force and/or strain of deflectable finger 540. In some examples, the thickness of deflectable finger 540 may be in a range of about 0.02 mm to about 0.3 mm. In some examples, the thickness of deflectable finger 540 may be in a range of about 0.05 mm to about 0.15 mm, and in some example, the thickness of deflectable finger 540 may be approximately 0.10 mm.

In some examples, spoon shaped finger 540 has an elastic limit higher than 0.9% and a modulus less than 13000 ksi. In some examples, contact member 520 is a stamped contact member. For example, the contact member 520 may be formed by stamping a strip of material into the contact member. In some examples, contact member 520 may be formed of one or more of titanium alloy or beta Ti alloy material, such as beta Ti alloy strip. The beta Ti alloy may contain alloy elements such as Mo, Nb, Ta, Sn and Zr. The alloy can be Ti-15Mo, beta 21S, Ti15Mo5Zr3Al, beta C etc. The beta Ti alloy strip has to have beta phase fraction larger than 94%. The thickness of the beta Ti alloy strip is between 0.003" to 0.004" (about 0.076 mm to 0.102 mm). In some examples, the contact member 520 has an overlapping joint 548 where a first end of the contact member 520 overlaps a second end of the contact member 520. There may be a distance between wall end 523 and elbow 528. This distance, or gap in the outer wall, may allow the overlapping joint 548 to slide with respect to wall 522 such that the distance between wall end 523 and elbow 528 can change during insertion of contact member 520 into the housing. In some examples, this distance may be in the range of 0.025 millimeters (mm) to 0.26 mm before inserted within the housing, but that distance may decrease when installed into the housing. In one example, the pre-installed distance may be in the range of 0.050 mm to 0.100 mm, and in one example the pre-installed distance may be approximately 0.076 mm. In other words, this distance or gap between wall end 523 and elbow 528 may facilitate insertion of contact member 520 into the housing and retention during manufacturing of the device. In some examples, contact member 520 may be defined by a length 527 and a diameter 526, and a ratio of the length to diameter is less than 1:1. In some examples, contact member 520 may be defined by a length 527 and a diameter 526, and a ratio of the length to diameter is less than 1:2.

FIGS. 6A and 6B illustrate a stamped contact member 690. In some examples, stamped contact member 690 has a thickness 694 of about 0.05 mm to 0.13 mm. In some examples, contact member 690 may comprise of a titanium alloy strip, beta Ti alloy strip material, or a beta Ti alloy strip. The stamped contact member 690 is rolled into a tube to make the contact member with the three V-shaped electrical fingers.

FIGS. 7A-7D illustrate another example electrical contact 750 configured to be disposed within the connector header 220 of the IMD 210 of FIG. 2. The electrical contact 750 provides an electrical connection between the IMD 210 and the lead 230. Electrical contact 750 may be defined in part by a length 746 and an outer diameter 748. In some examples, the length 746 to diameter 748 ratio may be 2:1. In some examples, the length 746 to diameter 748 ratio may be 2:1 or greater. In some examples, the length 746 to diameter 748 ratio may be 1:2. In some examples, electrical contact 750 may have a contact member 760 and a housing 770. Housing 770 may have a ring shape and may further have a housing interior 772 and defined in part by longitudinal axis 774. The housing interior 772 of the housing 770 may be configured to receive the contact member 760 therein.

The contact member 760 may have a general ring shape having a ring shaped wall 762 defined in part by an inner diameter and an outer diameter, and may be further defined by a contact longitudinal axis 758. In some examples, contact longitudinal axis 758 may be aligned with the housing longitudinal axis 774.

Contact member 760 may include at least one deflectable finger 780 extending from the ring shaped wall 762 at a hinge portion 778 to a distal end 779. The at least one deflectable finger 780 may be coupled with the ring shaped wall 762 at the hinge portion 778, and the at least one deflectable finger 780 may pivot along at least the hinge portion 778. In some examples, the at least one deflectable finger 780 may deflect along the finger itself. In some examples, the at least one deflectable finger 780 may have a curved shape. In some examples, the at least one deflectable finger 780 may have a curve of about 0.025 inches (0.635 mm), or less. In some examples, a clearance gap 752 may surround a portion of the at least one deflectable finger 280, as shown in FIG. 7C. In some examples, the distal end 779 of the at least one deflectable finger 780 may be disposed away from ring shaped wall 762 toward the contact longitudinal axis 758, and the distal end 779 may extend into the contact opening 764. In some examples, contact member 760 may include at least one deflectable V-shaped finger 780 extending from the ring shaped wall 762 into the contact opening 764, and having side edges 784A, 784B. In some examples, side edges 784A, 784B may be disposed at an angle relative to a central axis 782 of the at least one deflectable V-shaped finger 780. In some examples, the at least one deflectable V-shaped finger 780 is defined in part by a central axis 782, and the central axis is perpendicular to the housing longitudinal axis 774. In some examples, side edges 784A, 784B may be disposed at an angle relative to the housing longitudinal axis 774. In some examples, one or more side edges 784A, 784B may be disposed at a 45 degree angle to an insertion direction of the lead into the electrical contact, where the insertion direction may be aligned with the contact longitudinal axis 758. In some examples, one or more side edges 784A, 784B may be disposed at a 30-60 degree angle to an insertion direction of the lead into the electrical contact, where the insert direction may be aligned with the contact longitudinal axis 158.

In some examples, contact member 760 may include three deflectable V-shaped fingers 780A, 780B, 780C that extend from ring shaped wall 762 into contact opening 764. In some examples, three V-shaped fingers 780A, 780B, 780C are self-centering for a lead inserted into the electrical contact. In some examples, the three V-shaped fingers 780A, 780B, 780C are symmetrically disposed around the ring shaped wall 762. In some examples, the at least one deflectable V-shaped finger 780 comprises at least two deflectable V-shaped fingers that are self-centering for leads inserted into the electrical contact 750. In one or more examples, the deflectable V-shaped finger 780 has a spring bias configured to bias the finger 780 against a contact 240 (FIG. 2) of the lead 730. In some examples, the V-shaped finger 780 extends from a hinge portion 778 to a distal portion 779, where the distal portion 779 is configured to contact the contact 240 of the lead 230. In some examples, V-shaped fingers may extend to a distal end 779, and the distal ends 779 may extend away from wall 762 toward the contact longitudinal axis 758 and may define a distal end diameter 756. In some examples, the distal end diameter 756 may be smaller than an outer diameter of lead 730. In some examples, the lead 730 may deflect the distal end 779 of V-shaped fingers 780A, 780B, 780C toward wall 762. In some examples, V-shaped finger 780 has an elastic limit higher than 0.9% and a modulus less than 13000 ksi. In some examples, V-shaped finger 380 has an elastic limit higher than 0.9% and a modulus less than 12000-14000 ksi.

In some examples, fingers 780 and housing 770 of electrical contact 750 are electrically conductive. In some examples, electrical contact 750 may be coupled to conductive wires that run to the circuitry within the IMD, e.g., via a weld, solder or braze connection.

In some examples, contact member 760 is a stamped contact member. For example, the contact member 760 may be formed by stamping a strip of material into the contact member. In some examples, contact member 760 may be formed of one or more of titanium alloy or beta Ti alloy material, such as beta Ti alloy strip.

Figure 8A:
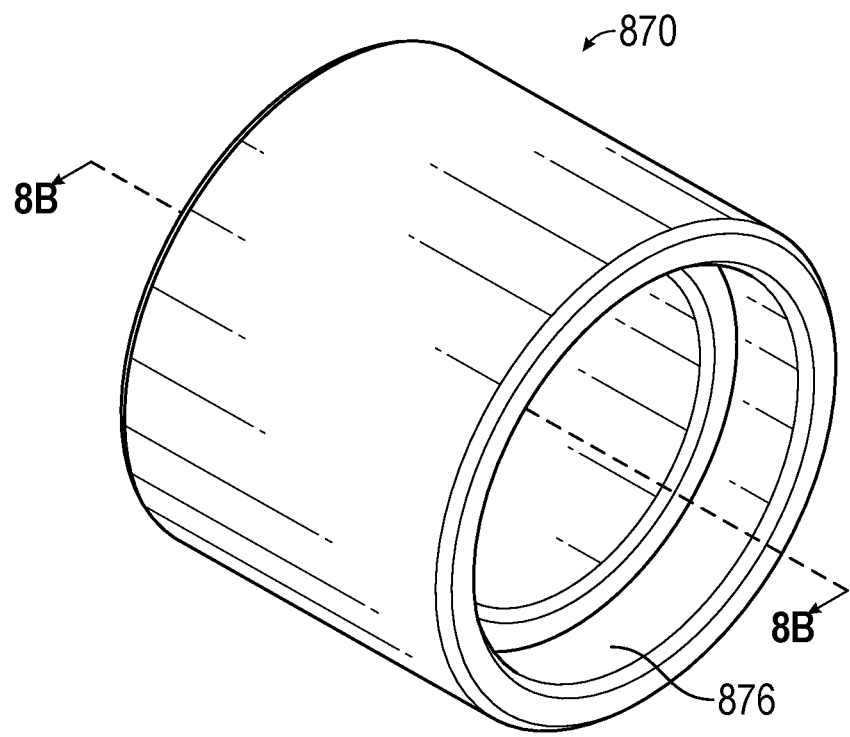
FIG. 8A is a conceptual diagram illustrating a housing for an electrical contact for an implantable medical device (IMD) in accordance with one or more techniques of this disclosure.
Figure 8B:
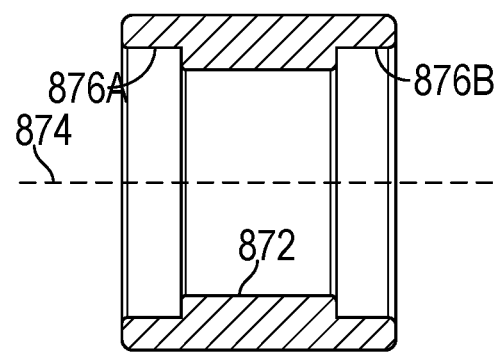
FIG. 8B is a cross-sectional view illustrating a housing for an electrical contact for an implantable medical device (IMD) in accordance with one or more techniques of this disclosure.

FIGS. 8A and 8B illustrate an example housing 870. Housing 870 may be formed of metallic material, for example by machining. In some examples, housing 870 may be formed of Titanium. Housing 870 may have a ring shape and may further having a housing interior 872 and defined in part by longitudinal axis 874. The housing interior 872 of the housing 870 may be configured to receive the contact member 760 (FIG. 7C), and the longitudinal axis 874 may be aligned with a longitudinal axis of the contact member. In some examples, housing 870 may be modified to accommodate varying lengths of the contact member. In some examples, housing 870 may include one or more counterbores. In some examples, housing 870 may include counterbore 876A at a first end of the housing and a second counterbore 876B at a second end of the housing 870.

Figure 9:
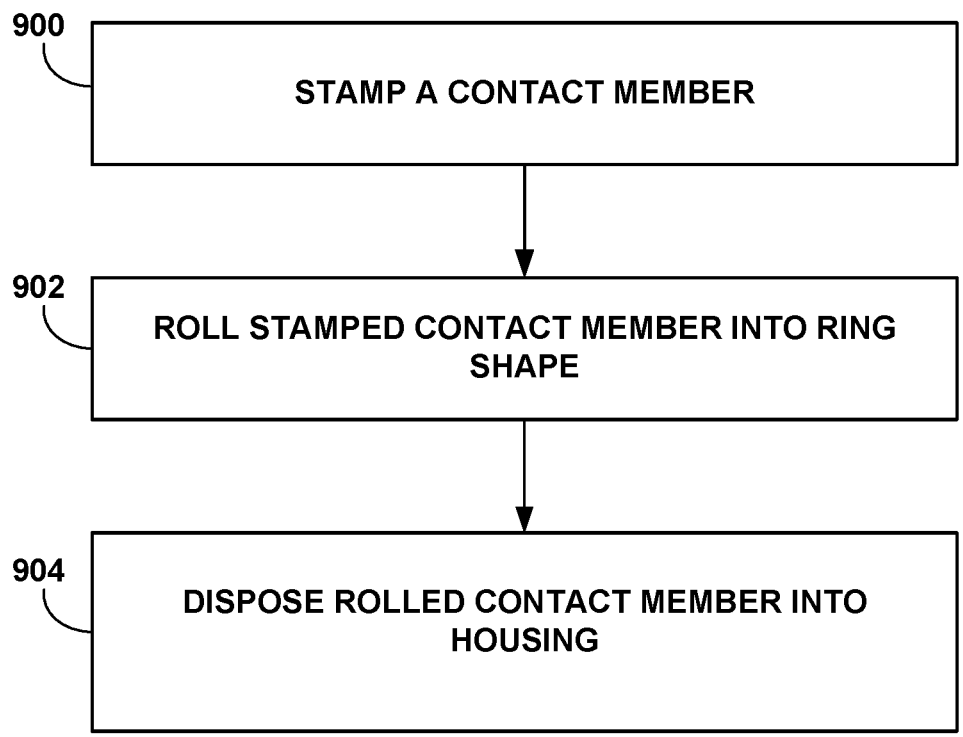
FIG. 9 is a flow diagram illustrating assembly of an electrical contact in accordance with one or more techniques of this disclosure.

FIG. 9 is a flow diagram illustrating fabricating an electrical contact. The electrical contact may include a contact member assembled within a housing. A strip of electrically conductive material, such as metallic material, may be used to form the contact member. In some examples, the strip of material may have a thickness of 0.05 mm to 0.15 mm. In some examples, the strip of material may include titanium alloy material. In some examples, the strip of material may include a beta Ti alloy strip.

A die may be used to stamp a contact member (900) from the strip of material, to form a stamped strip 690, as shown in FIGS. 6A, 6B. As shown, the stamped contact member 690 may include three V-shaped fingers 680. In some examples, the V-shaped fingers are processed to provide a beveled edge along the sides of the fingers. In some examples, high pressure stamping die may cause plastic deformation to edges and provides a beveled or rounded edge. In some examples, the V-shaped fingers are formed into shape where V-shaped members are bent away from the planar strip. In some examples, progressive die stamping may be used to create a bend and/or radius in the V-shaped fingers. In some examples, stamped contact member 690 has a thickness 694 of about 0.05 mm to 0.13 mm. In some examples, contact member 690 may comprise of a titanium alloy strip, beta Ti alloy strip material, or a beta Ti alloy strip.

The stamped contact member 690 may be rolled into a ring shape (902), for example a ring shape as shown in FIGS. 5A-5C. In some examples, rolling the stamped contact member 690 may include overlapping a portion of a first end 696 of the stamped contact member 690 over a second end 698 of the stamped contact member 690. In one or more examples, the stamped contact member 690 is rolled into a ring shape and secured in place, for example the stamped contact member 690 may be overlapped at 568 (FIG. 5) welded at a weld joint. The method further may include disposing the rolled contact member into a housing to form an electrical contact (904). The electrical contact 250 may further be disposed within a terminal 222 within a connector header 220 of an IMD 210 (FIG. 2) to facilitate the electrical connection between the lead 230 and the IMD 210 when the lead 230 is disposed within the terminal of the IMD 210.

The following examples are described herein.

Example 1: A electrical contact for coupling a contact of a medical lead with electronics of a medical device configured to deliver electrical stimulation therapy, the electrical contact includes a contact member having a ring shaped wall defined by a ring inner diameter and ring outer diameter, the contact member having at least one deflectable finger extending radially inward from the ring shaped wall into a contact opening defined by the ring inner diameter of the ring shaped wall; a housing having a ring shape defining an opening therein, the opening configured to receive the contact member therein, wherein the housing is defined in part by a housing longitudinal axis and a housing inner diameter; the contact member defined in part by a contact longitudinal axis, the contact longitudinal axis aligned with the housing longitudinal axis; and wherein the finger extends to a distal end and has side edges, the side edges of the finger disposed at respective angles relative to the housing longitudinal axis.

Example 2: The electrical contact of example 1, wherein the side edges of the finger are disposed at a 45 degree angle to an insertion direction of the lead into the electrical contact.

Example 3: The electrical contact of any of examples 1 and 2, wherein the at least one finger comprises at least two fingers, and the at least two fingers are self-centering for leads inserted into the electrical contact.

Example 4: The electrical contact of any of examples 1 through 3, wherein the contact member is a stamped contact member.

Example 5: The electrical contact of example 4, wherein a thickness of the stamped contact member is between 0.05 to 0.13 mm.

Example 6: The electrical contact of any of examples 1 through 5, wherein the contact member comprises titanium alloy material.

Example 7: The electrical contact of any of examples 1 through 6, wherein the contact member comprises a beta Ti alloy strip.

Example 8: The electrical contact of any of examples 1 through 7, wherein the finger has an elastic limit higher than 0.9% and a modulus range between 12000-14000 ksi.

Example 9: The electrical contact of any of examples 1 through 8, wherein the at least one finger comprises at least three deflectable fingers extending from the ring shaped wall.

Example 10: The electrical contact of any of examples 1 through 9, wherein the contact member is defined in part by a length and diameter, and a ratio of the length to diameter is less than 1:1.

Example 11: The electrical contact of any of examples 1 through 10, wherein the contact member is defined in part by a length and diameter, and a ratio of the length to diameter is less than 1:2.

Example 12: The electrical contact of any of examples 1 through 11, wherein the contact member is welded with the housing.

Example 13: The electrical contact of any of examples 1 through 12, wherein the deflectable finger has a spring bias configured to bias the deflectable finger against the contact of the lead.

Example 14: The electrical contact of any of examples 1 through 13, wherein the finger extends from a hinge portion to the distal end.

Example 15: The electrical contact of any of examples 1 through 14, wherein the finger is defined in part by a central axis, and the central axis of the finger is perpendicular to the housing longitudinal axis.

Example 16: The electrical contact of any of examples 1 through 15, wherein the at least one finger is V-shaped.

Example 17: The electrical contact of any of examples 1 through 16, wherein the at least one finger comprises a rounded end and a neck proximal from the rounded end, wherein the neck is narrower than the rounded end, and wherein the rounded end comprises a curved surface.

Example 18: An implantable medical device configured to deliver electrical stimulation therapy, the medical device includes an electronics housing having a connector header; an electrical contact disposed within the connector header, the electrical contact configured for coupling a medical lead with electronics of a medical device configured to deliver electrical stimulation therapy; the electrical contact includes a contact member having a ring shaped wall defined by a ring inner diameter and ring outer diameter, the contact member having at least one deflectable finger extending radially inward from the ring shaped wall into a contact opening defined by the ring inner diameter of the ring shaped wall; a housing having a ring shape defining an opening therein, the opening configured to receive the contact member therein, wherein the housing is defined in part by a housing longitudinal axis and a housing inner diameter; the contact member defined in part by a contact longitudinal axis, the contact longitudinal axis aligned with the housing longitudinal axis; and wherein the deflectable finger extends to a distal end and has side edges, the side edges of the deflectable finger disposed at respective angles relative to the housing longitudinal axis.

Example 19: The medical device of example 18, wherein a proximal end of the medical lead is disposed within the connector header and includes a contact configured to engage the contact member.

Example 20: The medical device of any of examples 18 and 19, wherein the contact member comprises titanium alloy material.

Example 21: The medical device of any of examples 18 through 20, wherein the finger has an elastic limit higher than 0.9% and a modulus range between 12000-14000 ksi.

Example 22: The medical device of any of examples 18 through 21, wherein the contact member comprises a plurality of contact members, arranged at different position to engage respective proximal lead contacts of a plurality of proximal lead contacts.

Example 23: The medical device of any of examples 18 through 22, wherein the at least one finger is V-shaped.

Example 24: The medical device of any of examples 18 through 23, wherein the at least one finger comprises a rounded end and a neck proximal from the rounded end, wherein the neck is narrower than the rounded end, and wherein the rounded end comprises a curved surface.

Example 25: A method for forming an electrical contact includes stamping a contact member from a strip of material and forming at least one deflectable finger; forming the stamped contact member into a ring shaped wall defined by a ring inner diameter and ring outer diameter, and the at least one deflectable finger extending radially inward from the ring shaped wall into a contact opening defined by the ring inner diameter of the ring shaped wall; and disposing the formed contact member within an electrical contact of a medical device.

Example 26: The method of example 25, further comprising disposing the contact member within a housing and welding the contact member to the housing.

Example 27: The method of any of examples 25 and 26, wherein forming the stamped contact member comprises forming the at least one deflectable finger into a V-shaped finger.

Example 28: The method of any of examples 25 through 27, wherein forming the stamped contact member comprises forming the at least one deflectable finger to comprise a rounded end and a neck proximal from the rounded end, wherein the neck is narrower than the rounded end, and wherein the rounded end comprises a curved surface.

Example 29: A electrical contact for coupling a contact of a medical lead with electronics of a medical device configured to deliver electrical stimulation therapy, the electrical contact includes a contact member having a ring shaped wall defined by a ring inner diameter and ring outer diameter, the contact member having at least one deflectable finger extending radially inward from the ring shaped wall into a contact opening defined by the ring inner diameter of the ring shaped wall; the contact member defined in part by a contact longitudinal axis; and wherein the finger extends to a distal end and has side edges, the side edges of the finger disposed at respective angles relative to the contact longitudinal axis.

Example 30: The electrical contact of example 29, wherein the side edges of the finger are disposed at a 45 degree angle to an insertion direction of the lead into the electrical contact.

Example 31: The electrical contact of any of examples 29 and 30, wherein the at least one finger comprises at least two fingers, and the at least two fingers are self-centering for leads inserted into the electrical contact.

Example 32: The electrical contact of any of examples 29 through 31, wherein the contact member has at least three deflectable fingers extending from the ring shaped wall.

Example 33: The electrical contact of any of examples 29 through 32, wherein the at least one finger is V-shaped.

Example 34: The electrical contact of any of examples 29 through 33, wherein the at least one finger comprises a rounded end and a neck proximal from the rounded end, wherein the neck is narrower than the rounded end, and wherein the rounded end comprises a curved surface.

Example 35: An implantable medical device configured to deliver electrical stimulation therapy, the medical device includes an electronics housing having a connector header; an electrical contact disposed within the connector header, the electrical contact configured for coupling a medical lead with electronics of a medical device configured to deliver electrical stimulation therapy; the electrical contact includes a contact member having a ring shaped wall defined by a ring inner diameter and ring outer diameter, the contact member having at least one deflectable finger extending radially inward from the ring shaped wall into a contact opening defined by the ring inner diameter of the ring shaped wall; the contact member defined in part by a contact longitudinal axis; and wherein the finger extends to a distal end and has side edges, the side edges of the finger disposed at respective angles relative to the contact longitudinal axis.

Example 36: The medical device of example 35, wherein a proximal end of the medical lead is disposed within the connector header and includes a contact configured to engage the contact member.

Example 37: The medical device of any of examples 35 and 36, wherein the finger has an elastic limit higher than 0.9% and a modulus range between 12000-14000 ksi.

Example 38: The medical device of any of examples 35 through 37, wherein the contact member comprises a plurality of contact members, arranged at different position to engage respective proximal lead contacts of a plurality of proximal lead contacts.

Example 39: The medical device of any of examples 35 through 38, wherein the contact member comprises a ring-shaped stamped contact member having an overlapping joint.

Example 40: The medical device of any of examples 35 through 39, wherein the at least one finger is V-shaped.

Example 41: The medical device of any of examples 35 through 40, wherein the at least one finger comprises a rounded end and a neck proximal from the rounded end, wherein the neck is narrower than the rounded end, and wherein the rounded end comprises a curved surface.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A electrical contact for coupling a contact of a medical lead with electronics of a medical device configured to deliver electrical stimulation therapy, the electrical contact comprising:
   a contact member having a ring shaped wall defined by a ring inner diameter and ring outer diameter, the contact member having at least one deflectable finger extending radially inward from the ring shaped wall into a contact opening defined by the ring inner diameter of the ring shaped wall;
   a housing having a ring shape defining an opening therein, the opening configured to receive the contact member therein, wherein the housing is defined in part by a housing longitudinal axis and a housing inner diameter;
   the contact member defined in part by a contact longitudinal axis, the contact longitudinal axis aligned with the housing longitudinal axis;
   wherein the at least one deflectable finger has a spring bias configured to bias the at least one deflectable finger against the contact of the lead; and
   wherein the at least one deflectable finger extends to a distal end and has side edges, the side edges of the at least one deflectable finger disposed at respective angles relative to the housing longitudinal axis.

2. The electrical contact of claim 1, wherein the side edges of the at least one deflectable finger are disposed at a 45 degree angle to an insertion direction of the lead into the electrical contact.

3. The electrical contact of claim 1, wherein the contact member is a stamped contact member.

4. The electrical contact of claim 3, wherein a thickness of the stamped contact member is between 0.05 to 0.13 mm.

5. The electrical contact of claim 1, wherein the contact member comprises titanium alloy material.

6. The electrical contact of claim 1, wherein the at least one deflectable finger has an elastic limit higher than 0.9% and a modulus range between 12000-14000 ksi.

7. The electrical contact of claim 1, wherein the at least one deflectable finger comprises at least three deflectable fingers extending from the ring shaped wall.

8. The electrical contact of claim 1, wherein the contact member is defined in part by a length and diameter, and a ratio of the length to diameter is less than 1:1.

9. The electrical contact of claim 1, wherein the at least one deflectable finger extends from a hinge portion to the distal end.

10. The electrical contact of claim 1, wherein the at least one deflectable finger is V-shaped.

11. The electrical contact of claim 1, wherein the at least one deflectable finger comprises a rounded end and a neck proximal from the rounded end, wherein the neck is narrower than the rounded end, and wherein the rounded end comprises a curved surface.

12. An implantable medical device configured to deliver electrical stimulation therapy, the medical device comprising:
   an electronics housing having a connector header;
   an electrical contact disposed within the connector header, the electrical contact configured for coupling a medical lead with electronics of a medical device configured to deliver electrical stimulation therapy;
   the electrical contact comprising:
   a contact member having a ring shaped wall defined by a ring inner diameter and ring outer diameter, the contact member having at least one deflectable finger extending radially inward from the ring shaped wall into a contact opening defined by the ring inner diameter of the ring shaped wall;
   a housing having a ring shape defining an opening therein, the opening configured to receive the contact member therein, wherein the housing is defined in part by a housing longitudinal axis and a housing inner diameter;
   the contact member defined in part by a contact longitudinal axis, the contact longitudinal axis aligned with the housing longitudinal axis;
   wherein the at least one deflectable finger has a spring bias configured to bias the deflectable finger against the contact of the lead; and
   wherein the at least one deflectable finger extends to a distal end and has side edges, the side edges of the at least one deflectable finger disposed at respective angles relative to the housing longitudinal axis.

13. The medical device of claim 12, wherein a proximal end of the medical lead is disposed within the connector header and includes a contact configured to engage the contact member.

14. The medical device of claim 12, wherein the contact member comprises titanium alloy material.

15. The medical device of claim 12, wherein the contact member comprises a plurality of contact members, arranged at different position to engage respective proximal lead contacts of a plurality of proximal lead contacts.

16. The medical device of claim 12, wherein the at least one deflectable finger comprises a rounded end and a neck proximal from the rounded end, wherein the neck is narrower than the rounded end, and wherein the rounded end comprises a curved surface.

17. A method for forming an electrical contact comprising:
   stamping a contact member from a strip of material and forming at least one deflectable finger;
   forming the stamped contact member into a ring shaped wall defined by a ring inner diameter and ring outer diameter, and the at least one deflectable finger extending radially inward from the ring shaped wall into a contact opening defined by the ring inner diameter of the ring shaped wall; and disposing the formed contact member within an electrical contact of a medical device.

18. The method of claim 17, further comprising disposing the contact member within a housing and welding the contact member to the housing.

19. The method of claim 17, wherein forming the stamped contact member comprises forming the at least one deflectable finger to comprise a rounded end and a neck proximal from the rounded end, wherein the neck is narrower than the rounded end, and wherein the rounded end comprises a curved surface.

20. The electrical contact of claim 1, wherein the at least one deflectable finger extends radially inward from the ring shaped wall in a circumferential direction.

21. The medical device of claim 12, wherein the at least one deflectable finger extends radially inward from the ring shaped wall in a circumferential direction.

\* \* \* \* \*